United States Patent
Mallee et al.

(10) Patent No.: US 7,977,066 B2
(45) Date of Patent: Jul. 12, 2011

(54) METHOD FOR PREPARING TRYPTOPHAN RICH PEPTIDES

(75) Inventors: Leon Franciscus Mallee, Utrecht (NL);
Petronella Wilhelmina Josephina Rosa Caessens, Wageningen (NL); Johannes Wilhelmus Leonardus Boumans, Ouderkerk aan de Amstel (NL)

(73) Assignee: Campina Melkunie B.V., Zaltbommel (NL)

( * ) Notice: Subject to any disclaimer, the term of this patent is extended or adjusted under 35 U.S.C. 154(b) by 0 days.

(21) Appl. No.: 12/256,951

(22) Filed: Oct. 23, 2008

(65) Prior Publication Data

US 2009/0105120 A1    Apr. 23, 2009

Related U.S. Application Data

(62) Division of application No. 10/433,798, filed as application No. PCT/NL00/00900 on Dec. 6, 2000, now abandoned.

(51) Int. Cl.
*C12P 21/06* (2006.01)
*A23C 21/02* (2006.01)
*A61K 38/02* (2006.01)

(52) U.S. Cl. .......... 435/68.1; 426/41; 426/583; 514/1.1; 514/5.6

(58) Field of Classification Search ............... 435/68.1; 426/41, 583; 514/1.1, 5.6
See application file for complete search history.

(56) References Cited

U.S. PATENT DOCUMENTS

| 4,485,040 A | 11/1984 | Roger et al. |
| 4,486,282 A * | 12/1984 | Bier ............................. 204/529 |
| 5,888,552 A | 3/1999 | Bounous et al. |

FOREIGN PATENT DOCUMENTS

| DE | 4130284 A1 | 3/1993 |
| FR | 2 671 351 | 7/1992 |
| JP | 02279700 A | 11/1990 |
| JP | 2000-001500 | 1/2000 |

OTHER PUBLICATIONS

ExPaSy Peptide Cutter. Pepsin Digestion on Alpha-lactalbumin (NP 776803), pp. 1-2, (2007).
NCBI Sequence Viewer, V. 2.0., NP 776803: Alpha-lactalbumin, pp. 1-3, (2007).
English Translation of DE 4130284 A1, 2008, pp. 1-2.
Markus, et al., "The Bovine Protein a-lactalbumin Increases the Plasma Ration of Tryptophan to the Other Large Neutral Amino Acids, and in Vulnerable Subjects Raises Brain Serotonin Activity, Reduces Cortisol Concentration, and Improves Mood Under Stress," *The American Journal of Clinical Nutrition*, vol. 71, No. 6, 2000, pp. 1536-1544.

* cited by examiner

*Primary Examiner* — Taeyoon Kim
(74) *Attorney, Agent, or Firm* — Gilberto M. Villacorta; Sunit Talapatra; Foley & Lardner LLP

(57) ABSTRACT

Described is a method for selectively isolating tryptophan containing peptides from an aqueous peptide mixture, including the steps of controlling the pH of the aqueous peptide mixture to 4.0-6.0, forming a precipitate of tryptophan containing peptides, and isolating the precipitated peptides.
The aqueous peptide mixture is preferably obtained by enzymatic cleavage at acidic pH of a protein source. Further, peptides having a Trp content of 8-15 w/w % and the use thereof as a food additive and as an active ingredient in a medicament are described.

22 Claims, 1 Drawing Sheet

METHOD FOR PREPARING TRYPTOPHAN RICH PEPTIDES

TECHNICAL FIELD OF THE INVENTION

The invention relates to a method for selectively isolating tryptophan (Trp) containing peptides from an aqueous mixture, to the tryptophan enriched peptides obtainable by the method and to the use of said peptides as food additive and medicament.

DESCRIPTION OF RELATED ART

Tryptophan is one of the amino acids that are used for the production of proteins by organisms, including human. Tryptophan is one of the less prominent amino acids in the food of the western world; the daily amount of tryptophan consumed is about 1 gram a day.

Tryptophan acts indirectly on the central nervous system; about 1% of the tryptophan of the consumed food is converted in the brain into the synaptic transmitter serotonin (Herderich and Gutsche, Food Rev Int 1997; 13:103-35). Serotonin plays an important role in several biological processes such as the state of mind, the appetite and pain perception (Young, The clinical psychopharmacology of tryptophan. In: Nutrition and the brain. Vol. 7. Eds: Wurtman R J, Wurtman J J Raven Press, New York, pp 49-88). In addition, serotonin plays a key role in the process of sleep (Hartmann E, Greenwald D, Tryptophan and human sleep: an analysis of 43 studies. In: Progress in tryptophan and serotonin research. Eds: Schlossberger H G, Kochen W. Walter de Gruyter & Co, Berlijn, Duitsland, pp 297-304; Schneider-Helmert D, Spinweber C L. Psychopharmacol 1986; 89:1-7; Cunliffe et al. Eur J Clin Nutr 1998; 52:425-30). As, in contrast to the precursor tryptophan, serotonin is not capable of passing the blood-brain barrier, the serotonin synthesis in the brain is dependent on the transport of tryptophan from the blood to the central nervous system (Fernstrom J D. J Nutr 1988; 118:1417-19). Research in animals and in humans has revealed that the amount of tryptophan in the brain, and therewith the serotonin production, is dependent on the amount of tryptophan circulating in the blood.

At normal conditions, the influx of tryptophan into the brain is not only dependent on the tryptophan level in the blood. The ratio between tryptophan and the other large neutral amino acids (LNAA) in the blood is also important. LNAAs are defined as Leucine (Leu), Valine (Val), Isoleucine (Ile), Tyrosine (Tyr), Phenylalanine (Phe) and Methionine (Met) (Heine, 1995, Supra). These LNAAs use a similar transport mechanism to pass the blood-brain barrier. The higher the ratio tryptophan/LNAAs in the blood, the more tryptophan can be transported to the central nervous system, and the more serotonin is produced in the brain (Herderich and Gutsche, Supra).

Consumption of pure tryptophan leads to a higher ratio between tryptophan and LNAAs in the blood, and, in this way, induces the above described neurological effects. The use of pure tryptophan in commercial products such as functional foods is however subject to strict regulations which may vary per country. In order to change the above mentioned ratio in a positive way, this must therefor be achieved by changes in the pattern of food consumption; protein-rich food leads to decrease of the said ratio, as tryptophan is one of the less available amino acids (Fernstrom and Fernstrom. Am J Clin Nutr 1995; 61:312-29). Food, rich in carbohydrates increases the said ratio. Sugars, such as glucose, increase the release of insulin by the pancreas. Insulin stimulates the uptake of LNAA in the muscle tissue, whereby the ratio between tryptophan and LNAA in the blood increases (Young, Supra).

Proteins in food contain actually too little tryptophan to bring about the above mentioned effects on the central nervous system. The protein α-lactalbumin is an ingredient of whey and is the best known tryptophan source in food; it consists of 123 amino acids, four of which being tryptophan residues. This is about 6 g tryptophan per 100 g protein (Heine et al. J Nutr 1991; 121:277-83). The catabolism of α-lactalbumin in the intestine is however slow and leads to a very slow uptake of the tryptophan (Scanff et al. J Agric Food Chem 1990; 38:1623-29). The desired (substantial) change in the ratio between tryptophan and LNAA in the blood, and therewith the positive effects of tryptophan on the central nervous system, do not occur. Proteins can be fragmented into peptides that consist of a small number of amino acids. Peptides that are formed after fragmenting whey proteins are usually faster and easier digestible than the parent protein (Nakano et al. J Japanese Soc Nutr Food Sci 1994; 47:195-201).

For the above reasons, there is a need in the art for readily available tryptophan rich peptides.

In the past, several methods have been developed to increase the Trp-levels in protein products. E.g., EP 22696 by INRA, which describes a method to purify alfa-lactabumin; WO 91/10441 (Medgennix) describes a composition characterized in that it comprises a polypeptide having a high content of Trp, and arginin and/or ornithin. WO 98/14204 (Laboratoires Oenobiol) describes novel uses of alfa-lactalbumin and compositions containing it, as a nutritional complement and as medicine for regulating sleep and the biological clock.

However, the above mentioned disclosures do not mention a method to increase the level of tryptophan in protein products other than by further purifying an intact protein already having a relatively high Trp content. Thus, the only way of the above art to supply an increased dosage of tryptophan to individuals is by administering a high amount of alfa-lactalbumin. The disadvantage of this method is that the ratio of Trp to LNAA is still too low as mentioned in the introduction. DE4130284 (Heine) describes the preparation of peptides containing tryptophan, however the level is still low and no specific purification is described. JP 2279700 (Asahi) reaches higher levels of tryptophan, but the method used requires addition of acetone in high amounts after enzymatic hydrolysis with a very high amount of pronase. In the food industry, the use of acetone is questionable; and the enzyme used is very expensive and therefore less suitable for use on large scale.

SUMMARY OF THE INVENTION

The present invention provides an improved method for selectively isolated tryptophan containing peptides from an aqueous peptide mixture, comprising the steps of:
 a) controlling the pH of the aqueous peptide mixture to 4.0-6.0, forming a precipitate of tryptophan containing peptides, and
 b) isolation of the precipitated peptides.

DETAILED DESCRIPTION OF PREFERRED EMBODIMENTS

Figure 1:
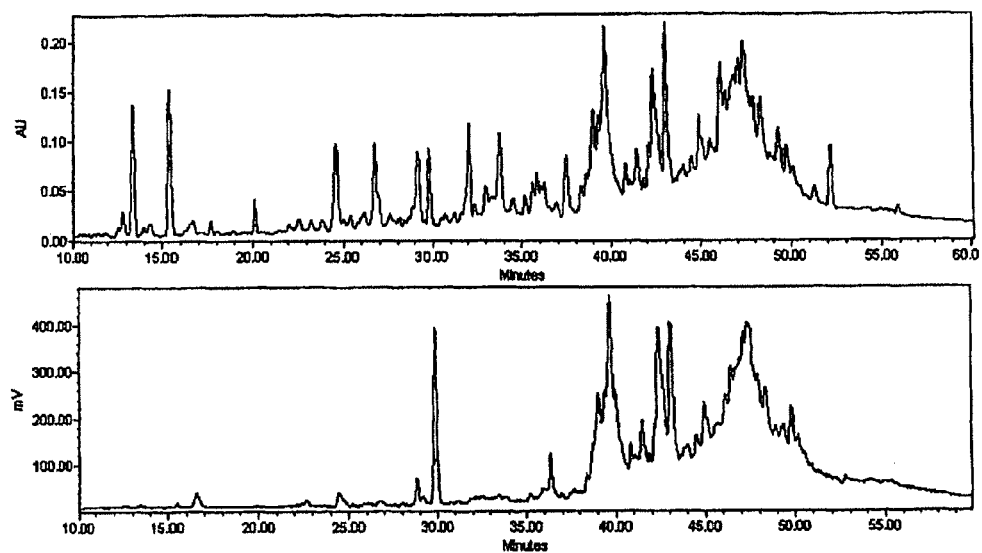
FIG. 1 shows the absorption at OD 214 nm signal (upper panel) and fluorescence signal (lower panel) of the peptide mixture from example 1.

Herein the term "peptides" relate to amino acid chains having a molecular weight of 500-5000 Dalton. It has surprisingly been found that when the pH of the aqueous peptide mixture is controlled at 4.0-6.0, preferably between 4.5-6.0 and most preferably around 5.0 (i.e. 4.7-5.3) tryptophan containing peptides precipitate, which precipitate can conveniently be used to isolate the tryptophan containing peptides. In the art, hydrolysis of proteins by mineral acids to obtain peptide mixtures was not recommended, as it was correlated with almost complete destruction of tryptophan (see W. Heine at al, Supra). "Controlling" of the pH means that the pH should be adjusted or kept at the above described pH value during the precipitation of the Trp containing peptides.

Isolation of the precipitated peptides can be done by methods that are known in the art. The precipitated peptides can e.g. be collected by centrifugation, decantation or filtration and the like. In order to obtain a long shelf life, the isolation preferably comprises a drying step. The skilled person is aware of suitable drying techniques.

Preferably, the precipitation is carried out at a temperature below 20° C. Below said temperature, tryptophan containing peptides have shown to precipitate very efficiently.

In a preferred embodiment, the aqueous peptide mixture is prepared by enzymatic cleavage of a protein source.

Preferably, the protein source is cleaved at acidic pH by one or more acid proteases or cysteine proteases, especially by one or more enzymes, chosen from the group, consisting of pepsine, rennin, acid fungal proteases, chymosin, papain, bromelain, chymopapain or ficin or mixtures of two or more thereof. By cleavage of a protein source by one or more of said acid proteases, especially pepsin at a pH between 1.5 and 3.5, preferably between 2-3, peptides having a hydrophobic nature are generated. It was found that from these peptide mixtures, the tryptophan containing peptides could very efficiently be selectively isolated by controlling the pH to 4.0-6.0, preferably to around 5.0. In case the pH at the enzymatic cleavage was below 4.0, the pH was to be adjusted to 4.0-6.0 in order to precipitate the tryptophan containing peptides. Preferably, the enzymatic activity is quenched by inactivation of the enzyme before the precipitation step. The skilled person will know how to inactivate the proteolytic enzyme. In case an enzyme is chosen having its pH optimum within the above mentioned pH range of 4.5-6.0, such as e.g. papaine or bromelaine, it will be possible to design the method according to the invention in such way that cleavage of the protein source and precipitation of the tryptophan containing peptides can occur simultaneously. Care has to be taken that the precipitation is done at conditions wherein the hydrolysed peptides preferentially precipitate; otherwise, a precipitate of partial hydrolysed peptides may be obtained.

Preferably, the peptide mixture is desalted before the step of controlling the pH (step a). It has been found that a desalting step prior to the pH controlling step leads to an improved yield of precipitated trp containing peptides. Desalting is a known technique and can be done by e.g. nanofiltration, ultrafiltration or electrodialysis. Especially when the peptides are obtained by enzymatic cleavage, desalting the obtained peptide mixture leads to improved yields. Desalting is preferably carried out such that 50-95% of the salt present during the cleavage reaction is removed from the peptide mixture.

Preferably, the tryptophan containing peptides are derived from whey protein. This means that preferably whey proteins are chosen as a protein source for the aqueous peptide mixture. Whey proteins have a relatively high Trp content (about 1.8 w/w %), rendering these proteins extremely suitable for the method according to the present invention. However, all tryptophan containing proteins can be used in the method according to the invention, although Trp rich proteins are preferred. In a very attractive embodiment of the invention, the tryptophan containing peptides are derived from α-lactalbumin enriched whey protein concentrate (WPC) or α-lactalbumin enriched whey protein isolate (WPI). Such isolates are derived from whey protein and have a high α-lactalbumin content. α-lactalbumin has a high Trp content of about 5.8 w/w %. A whey protein isolate containing about 60 w/w % α-lactalbumin can be obtained from DMV International, the Netherlands.

By the method of the invention, a peptide mixture can be obtained having a tryptophan content of 8-15 w/w % on peptide basis, that can advantageously be used in e.g. a food ingredient or a medicament. As food ingredient, the peptide mixture, obtainable by the present invention can e.g. be used as an ingredient (Trp source) for complete newborn nutrition formulas, such as substitute breastmilk powder. In order to bring the contents of such nutrition mix in conformity with natural mothermilk as much as possible, a high amount of Trp comprising peptides are needed in the formula. The peptides according to the present invention are excellent candidates.

It is known that Trp plays an important role as precursor in the synthesis of the neurotransmitters serotonin and triptamin as well as for the vitamin nicotinic acid and melatonin. As tryptophan starvation leads to serious problems in the synthesis of the above mentioned vital compounds, the peptides according to the present invention can advantageously be used in a human or veterinary medicament for inducing the synthesis of serotonin, tryptamine, nicotinic acid or melatonin.

Further, Trp-containing peptides are believed to be useful in cancer treatment (see e.g Panzer and Viljoen, 1997, J. Pineal Res 22: 184-202; Bubenik et al, 1998, Biological Signala and Receptors 7: 195-219; Blask et al, 1999, Biological Signala and Receptors 8: 49-55). Therefore, the peptide mixture according to the invention can be used as active ingredient in a medicament against malignant cell growth.

With the method of the present invention, a peptide mixture can be obtained, having a Trp/(Phe+Tyr) ratio of at least 0.900 on weight basis. As phenylalanine (Phe) and tyrosine (Tyr) are often competing with Trp in the uptake by the cells (Heine, Supra), it is very advantageous to have a Trp/(Phe+Tyr) ratio as high as possible, as Phe and Tyr are not limiting in the nutrition. It is known that for an effective administration of tryptophan, the ratio of tryptophan to large neutral amino acids should be as high as possible, as these large neutral amino acids (LNAA) compete with Trp in the uptake by the cells in the human and animal body (see above). The LNAA therefore inhibit the proper Trp uptake.

In another preferred embodiment, the peptides mixture according to the invention has therefore a Trp/Phe+Tyr+Leu+Val+Iso+Met) ratio of at least 0.25 on weight basis, rendering the peptide mixture extremely suitable for use as food ingredient or medicament. Because of the very low LNAA content, the tryptophan can be readily taken up by the human or animal body to which it is administered.

The tryptophan containing peptides can be identified in an aqueous peptide mixture and quantified by diluting the peptide mixture into a solution containing acetonitril and trifluoroacetic acid, separating the peptides into fractions, and measuring peptides specific light absorption and tryptophan specific fluorescence on each fraction.

The identification of tryptophan containing peptides is important to monitor the above mentioned preparation method and in order to be able to provide a quality control of the tryptophan content of a peptide mixture. The identification method is based on the fact that tryptophan exerts a specific fluorescence, which is not observed with other amino acids (see Heine, Supra). A combination of fluorescence measurement to establish the tryptophan content with a peptide specific measurement by UV-light absorption measurements is a very convenient way to obtain all the information that is needed to establish both the protein content (based on the absorption) and tryptophan content (based on the fluorescence data) of the fractions. For fractionation of the peptides, the peptides mixture is preferably diluted into a solution of 0.5-2 v/v % acetonitril and 0.05-0.25 w/w % trifluoracetic acid. In such a solution, the peptides can easily be separated by column chromatography, preferably on a reverse-phase column. For this, the solution preferably contains a 1 v/v % acetonitril and 0.1 w/w % trifluoracetic acid.

The peptide specific light absorption is measured at a wavelength of 214 nm.

The invention will now be further illustrated by some non-limiting examples.

Example 1

A 5% whey protein solution containing 45% α-Lactalbumin (DMV International, The Netherlands) is dissolved in demineralised water. The pH is adjusted to 2.0 using 1M hydrochloric acid. Hereafter the solution is heated to 50° C.

The hydrolytic reaction is started by adding 1% pepsin. After 6 hours the reaction is stopped by raising the pH to 5.0 and lowering the temperature to 10° C. After storage of 4 hours at this temperature, the tryptophan peptides are collected by centrifugation and subsequent freeze drying.

Tryptophan is determined using a specific technique based on total enzymatic hydrolysis (Garcia, S. E.; Baxter, J. H. (1992) Determination of tryptophan content in infant formulas and medical nutrition. *J. AOAC Int.* 75:1112-1119). The amino acids phenylalanine, tyrosine, leucine, isoleucine, valine and methionine are determined according EG guideline 98/64 (Sep. 3, 1998; publication L257/14-23 of Sep. 19, 1998). Protein is determined using the standard Kjeldahl method (IDF-FIL 20A, 1986). The resulting product contains 9.7% tryptophan on protein.

The calculated important rations of Trp/LNAA are listed in table 1.

TABLE 1

Amino acid ratios in α-whey and products prepared herefrom

| | Amino acid ratios (based on g/100 g product values) | |
|---|---|---|
| | Trp/(Phe + Tyr) | Trp/(Phe + Tyr + Leu + Val + Iso + Met) |
| Puridfied α-lactalbumin (Sigma) | 0.45 | 0.195 |
| Whey protein solution | 0.47 | 0.11 |
| Tryptophan-peptides | 0.97 | 0.32 |

Example 2

A whey protein isolate (WPI), containing 60% α-Lactalbumin (experimental product of DMV International, The Netherlands) is dissolved in an aqueous solution. The pH of the solution is adjusted using diluted phosphoric acid and heated to 45° C. Hydrolysis is started by adding 2% pepsin (Merck, 2500 FIP-U/g) and carried out for 2 hours. Reaction is stopped by pasteurising the solution at 85° C. for 10 minutes. Hereafter, the pH is raised to 5.5 and the solution is cooled to <15° C. After 10 hours, the tryptophan containing peptides are collected using microfiltration. Typically, a membrane having a nominal molecular weight cut-off of 1 μm is used. The peptides are hereafter spray dried. The resulting product contains 9.3% tryptophan on protein.

Example 3

A whey protein solution similar to example 1, was hydrolysed with pepsin (American Laboratories) using 0.25% and 0.75% E/S. After 5 hours, the reaction was stopped by raising the pH to 5.2 using 1.0M NaOH and cooling the solution to <15° C.

The precipitated peptides were harvested after 16 hours by centrifugation. The relevant analyses were done on both the precipitated tryptophan rich peptides and the supernatant. These are given in the table below.

TABLE 2

Tryptophan concentration and Trp/LNAA ratio of both fractions, precipitate and supernatant, after centrifugation.

| | 0.25% E/S | | 0.75% E/S | |
|---|---|---|---|---|
| | pellet | supernatant | pellet | Supernatant |
| Yield (%) | 12.1 | 87.9 | 11.4 | 88.6 |
| Protein content (%) | 74.3 | 71.6 | 72.6 | 74.3 |
| Trp content (g/Kg) | 70.6 | 24.9 | 70.5 | 23.7 |
| Trp/Protein | 10.5 | 3.4 | 10.7 | 3.1 |
| Trp/(Phe + Tyr) | 1.26 | 0.42 | 1.26 | 0.40 |
| Trp/(Phe + Tyr + Leu + Val + Iso + Met) | 0.35 | 0.10 | 0.35 | 0.10 |

Example 4

A 10% whey protein solution containing 45% α-Lactalbumin (DMV International, The Netherlands) is dissolved in demineralised water. The pH is adjusted to 7.0 using 1M sodium hydroxide. Hereafter the solution is heated to 50° C.

The hydrolytic reaction is started by adding 2% ENZECO Bromelain 240 (Enzyme Development Corporation). After 21 hours the reaction is stopped by heating the solution to 85° C. for 10 minutes. Following, the peptide mixture is cooled to room temperature, the pH adjusted to 4.5 using phosphoric acid and the temperature is lowered to 10° C. After storage during 12 hours at this temperature, the tryptophan peptides are collected by centrifugation and subsequent freeze drying.

The resulting tryptophan concentration of the peptides was 8%.

Example 5

100 lt of a 5% whey protein isolate solution (Davisco) is prepared and then hydrolysed using 2% Pepsin. The solution was hydrolysed for 12 hours at pH 3.0. The reaction was stopped by heating the solution to 80° C. for 30 minutes. Hereafter, the solution was ultrafiltered on a pilot NF unit using Celgard NF-PES-10 membrane. The pH of the retentate was controlled at 3.0 and the solution filtered up to 200% diafiltration.

After desalting, the pH of the retentate was adjusted to 5.5 and the solution is cooled to <10° C. to facilitate precipitation of the Tryptophan containing peptides. After 10 hours of storage, the precipitate was collected using centrifugation. Hereafter, the peptides were dried.

The tryptophan and protein concentration in the sample was respectively 9.5% and 91%. The composition of the peptides is listed in the table below.

TABLE 3

Amino acid ratios of Tryptophan rich peptide fraction

| | Amino acid ratios (based on g/100 g product values) | |
|---|---|---|
| | Trp/(Phe + Tyr) | Trp/(Phe + Tyr + Leu + Val + Iso + Met) |
| Whey protein solution | 0.47 | 0.11 |
| Tryptophan-peptides | 1.03 | 0.35 |

Example 6

HPLC specific for Tryptophan Peptides

A Reversed Phase HPLC-method (RPC) was set-up to identify and quantitate tryptophan containing peptides in a mixture of peptides, making use of the specific fluorescent properties of this amino acid.

A solution of was prepared of a mixture of peptides in binding buffer. These solutions were filtered using a 0.2 μm filter and then are analysed by reversed phase chromatography. A Widepore C18 5 μm RPC column (Baker) was used. The binding buffer consisted of demineriIsed water/0.1% TFA (trifluoroacetic acid) and the peptides were eluted using an acetonitril/0.083% TFA buffer (buffer B). The level of Buffer B was increased to 60% in 90 minutes, whereafter tightly bound material was removed by running 100% buffer for 20 minutes.

The peptides are detected by measuring absorption at 214 nm and fluorescence (excitation and emission wavelengths of respectively 290 nm and 340 nm).

Figure 2:
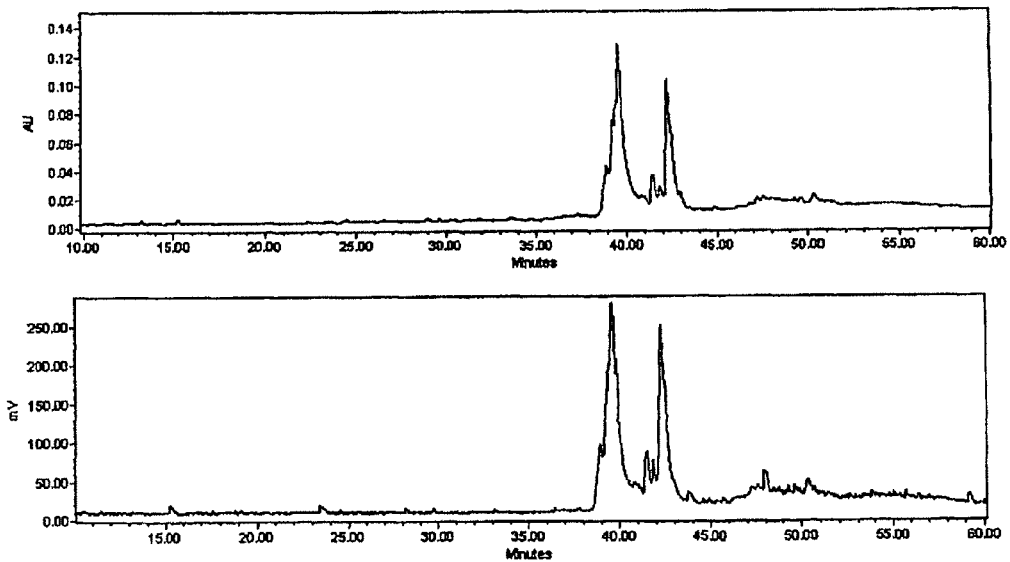
FIG. 2 shows the absorption at OD 214 nm signal (upper panel) and fluorescence signal (lower panel) of the tryptophan rich peptide fraction from example 1.

The peptide mixture after hydrolysis and the precipitated peptides from example 1 are listed in FIGS. 1 & 2.

Example 7

The peptides can be used in Infant formulas. A model recipe is as follows:

| Component | Concentration (g/lt) |
|---|---|
| Tryptophan rich peptides | 10.0 |
| Esprion 580 (DMV International) | 10.0 |
| Edible Lactose (DMV International) | 30.0 |
| Malto dextrin DE-20 | 23.0 |
| Corn Syrup Solids | 25.0 |
| Emulsifier (Sternphil E60; Stern) | 5.0 |
| Oil-mix (45% sunflower; 25% MCT; 30% soy-oil) | 40.0 |
| Calcium ortho phosphate | 1.8 |
| Calcium carbonate | 1.3 |
| Magnesium Chloride | 0.3 |
| Potassium Chloride | 0.4 |
| Tri-Sodium Citrate | 0.5 |
| Water | 852.7 |
| Total | 1000 |

The emulsifier is dissolved in the oil fraction. The peptides and carbohydrates are dissolved in part of the water of 70° C. Minerals are dissolved separately. The oil mixture in then added to the peptide/carbohydrate solution and mixed using a high shear mixer for 3 minutes.

The pre-emulsion is then homogenised twice at 250 bars. The formula can either be pasteurised by heating at 80° C. for 15 minutes and spray dried (powdered formula), or sterilised in bottles at 120° C. for 10 minutes (liquid formula).

Example 8

The peptides can be incorporated in an instant drink mix. The recipe contains:

| | |
|---|---|
| Tryptophan rich peptides | 15.0% |
| Whey protein concentrate 80 (Esprion 580; DMV International) | 60.0% |
| Glutamine Peptides (WGE80GPU; DMV International) | 10.0% |
| Glucodry (Corn Syrup Solids from Avebe) | 5.0% |
| Vitamin mix (Roche) | 4.90% |
| Cocoa powder (D-11-S, ADM Cocoa, The Netherlands) | 3.00% |
| Flavour; Vanilla JSH00712F, McCormick&Co. | 1.15% |
| Flavour; Chocolate fudge FF22034, McCormick&Co. | 0.95% |
| Sweetener (Aspartame, Nutrasweet) | 0.20% |
| Total | 100% |

The dry ingredient are mixed and then added to 118 ml water. The solution is mixed so that the components dissolve. One serving contains 35 g of powder mix supplying approximately 525 mg Tryptophan.

The invention claimed is:

1. A method for preparing a food product comprising tryptophan containing peptides, the method comprising the steps of:
   (a) obtaining an aqueous peptide mixture comprising whey protein,
   (b) controlling the pH of the aqueous peptide mixture to a pH between 4.0-6.0, forming a precipitate of tryptophan containing peptides,
   (c) isolating the precipitated peptides, and
   (d) incorporating the precipitated peptides into a food product.

2. The method according to claim 1, wherein step (b) is carried out at a temperature of below 20° C.

3. The method according to claim 1, wherein the aqueous peptide mixture is prepared by enzymatic cleavage of the whey protein.

4. The method according to claim 3, wherein the whey protein is enzymatically cleaved by one or more acid proteases or cysteine proteases selected from the group consisting of pepsin, papain and bromelain.

5. The method according to claim 4, wherein the whey protein is enzymatically cleaved by pepsin at a pH of between 1.5-3.5.

6. The method according to claim 1, wherein the peptide mixture is desalted.

7. The method of claim 3, wherein the whey protein comprises α-lactalbumin enriched whey protein.

8. A method for preparing a food product comprising a tryptophan enriched peptide mixture comprising the steps of:
   (a) providing an aqueous peptide mixture prepared from enzymatic cleavage of a protein source;
   (b) controlling the pH of the aqueous peptide mixture to about 4.0 to about 6.0 to form a precipitate of tryptophan-containing peptides;

(c) isolating the tryptophan-containing peptides from the precipitate to form the tryptophan enriched peptide mixture; and (d) incorporating the mixture into a food product.

9. The method according to claim 8, wherein step (b) is carried out at a temperature of below 20° C.

10. The method of claim 8, wherein the protein source is cleaved by at least one acid protease or cysteine protease selected from the group consisting of pepsin, papain or bromelain and combinations thereof.

11. The method of claim 8, wherein the protein source is cleaved by pepsin at a pH of between 1.5-3.5.

12. The method of claim 8, wherein the protein source is cleaved by pepsin at a pH of between 2-3.

13. The method according to claim 8, wherein the tryptophan enriched peptide mixture comprises a tryptophan content of 8-15 w/w % on peptide basis.

14. The method of claim 8, wherein the tryptophan enriched peptide mixture comprises a Trp/(Phe+Tyr) ratio of at least 0.900 on weight basis.

15. The method of claim 8, wherein the tryptophan enriched peptide mixture comprises a Trp/(Phe+Tyr+Lcu+Val+Iso+Met) ratio of at least 0.300 on weight basis.

16. The method of claim 8, further comprising the step of using the tryptophan enriched peptide mixture in a human or veterinary medicament as an active ingredient for inducing the synthesis of serotonin, tryptamine, nicotinic acid or melatonin.

17. The method of claim 8, further comprising the step of using the tryptophan enriched peptide mixture as an active ingredient in a medicament against cancer cell growth.

18. The method of claim 8, further comprising the step of desalting the aqueous peptide mixture prior to the step of controlling the pH.

19. The method according to claim 5, wherein the whey protein is cleaved by pepsin at a pH of between 2-3.

20. The method according to claim 1, wherein the food product is an infant formula.

21. The method according to claim 8, wherein the food product is an infant formula.

22. The method according to claim 8, wherein the food product is an medicament.

\* \* \* \* \*